United States Patent [19]

Cragoe, Jr. et al.

[11] Patent Number: 4,625,047
[45] Date of Patent: Nov. 25, 1986

[54] SUBSTITUTED (2,3-DIHYDRO-4-(3-OXO-1-CYCLOHEXEN-1-YL)PHENOXY) ALKANOIC ACIDS, THEIR DERIVATIVES AND THEIR SALTS

[75] Inventors: Edward J. Cragoe, Jr., Lansdale; Adolph M. Pietruszkiewicz, North Wales; Otto W. Woltersdorf, Jr., Chalfont, all of Pa.

[73] Assignee: Merck & Co., Inc., Rahway, N.J.

[21] Appl. No.: 812,669

[22] Filed: Dec. 23, 1985

[51] Int. Cl.$^4$ .............................................. C07C 69/76
[52] U.S. Cl. ...................................... 560/53; 562/463; 562/464
[58] Field of Search ................... 560/53; 562/463, 464; 514/543, 571

[56] References Cited

U.S. PATENT DOCUMENTS

| 4,337,354 | 6/1982 | Cragoe, Jr. et al. | 560/53 |
| 4,356,313 | 10/1982 | Cragoe et al. | 560/53 |
| 4,585,888 | 4/1986 | Urban | 560/53 |

FOREIGN PATENT DOCUMENTS 6125340  1/1981  Japan ................................ 560/53

OTHER PUBLICATIONS

"Agents for the Treatment of Brain Injury" 1. (Aryloxy) Alkanoic Acids, Cragoe et al., J. Med. Chem. (1982), 25 567-579.

Primary Examiner—Paul J. Killos
Attorney, Agent, or Firm—Charles M. Caruso; Daniel T. Szura; Hesna J. Pfeiffer

[57] ABSTRACT

The invention relates to novel substituted [2,3-dihydro-4-(3-oxo-1-cyclohexen-1-yl)phenoxy]-alkanoic acids their derivatives and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections and various brain concussions.

13 Claims, No Drawings

SUBSTITUTED (2,3-DIHYDRO-4-(3-OXO-1-CYCLOHEXEN-1-YL)PHENOXY) ALKANOIC ACIDS, THEIR DERIVATIVES AND THEIR SALTS

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cerebral infections and various concussions results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

A recent publication entitled *"Agents for the Treatment of Brain Injury"* 1. (Aryloxy)alkanoic Acids, Cragoe et al, J. Med. Chem., (1982) 25, 567–79, reports on recent experimental testing of agents for treatment of brain injury and reviews the current status of treatment of brain injury.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

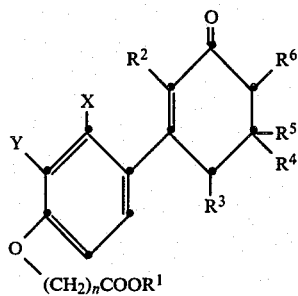

(I)

wherein:

$R^1$ is hydrogen, lower alkyl, branched or unbranched, containing from 1 to 5 carbon atoms such as methyl, ethyl, n-propyl, isopropyl and the like, or a carboxyalkyl group containing from 2 to 6 carbon atoms such as carboxymethyl, 1-carboxyethyl, 1-carboxy-1-methylethyl, 2-carboxyethyl, 1-carboxy-1-ethylpropyl and the like;

$R^2$, $R^6$ are each independently hydrogen or lower alkyl, branched or unbranched, containing from 1 to 5 carbon atoms;

$R^3$ is hydrogen, lower alkyl, branched or unbranched, containing from 1 to 5 carbon atoms, cycloalkyl containing from 3 to 6 nuclear carbon atoms such as cyclopropyl, cyclobutyl, cyclopentyl and the like, or aryl such as phenyl;

$R^4$, $R^5$ are each independently hydrogen, lower alkyl, branched or unbranched, containing from 1 to 5 carbon atoms, aralkyl such as benzyl, aryl such as phenyl, or halo substituted aryl such as p-fluorophenyl, o-fluorophenyl, p-chlorophenyl and the like;

X, Y are each independently hydrogen, halo or lower alkyl containing from 1 to 5 carbon atoms; and n is 1 to 4.

Positions 4,5 and 6 of the cyclohexene ring, when occupied by two different groups are asymmetric, therefore the compounds of the invention exhibit optical isomerism. If there is only one asymmetric atom the product consists of a racemate composed of two enantiomers. If there are two asymmetric atoms there will be two diasteriomers, each consisting of a racemate. Diasteriomers can be separated by physical means, e.g. chromatography. Racemic compounds or their precursors can be resolved so that the pure enantiomers can be prepared, thus the invention includes each pure diasteriomer and the corresponding pure enantiomers. This is an important point since some of the racemic diasteriomers consist of one racemate which is much more active than the other one and the same is true of the two enantiomers of each racemic diasteriomer. Furthermore, the less active diasteriomer and enantiomer generally possesses the same intrinsic toxicity as the more active diasteriomer and enantiomer. In addition, it can be demonstrated that the less active diasteriomer or enantiomer depresses the inhibitory action of the active enantiomer at the tissue level. Thus, for three reasons it is advantageous to use the pure, more active diasteriomer or enantiomer rather than the mixed diasteriomer or racemate.

Since the products of the invention are acidic, the invention also includes the obvious pharmaceutically acceptable salts, such as the sodium, potassium, ammonium, trimethylammonium, piperazinium, 1-methylpiperazinium, guanidinium, bis-(2-hydroxethyl)ammonium, N-methylglucosammonium and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily involves novel substituted [2,3-dihydro-4-(3-oxo-1-cyclohexen1-yl)phenoxy]alkanoic acids and their salts, it also includes their derivatives, such as oximes, hydrazones and the like. Additionally, this invention includes pharmaceutical compositions in unit dosage form containing a pharmaceutical carrier and an effective amount of a compound of Formula I, its pure diasteriomer and its pure (−) or (+) enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II:

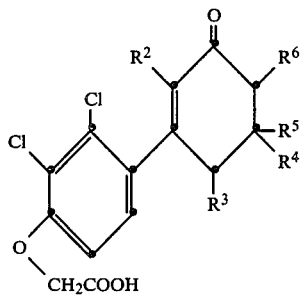

wherein:

$R^2$, $R^3$, $R^4$, $R^5$, $R^6$ are each independently hydrogen or lower alkyl, branched or unbranched, containing from 1 to 5 carbon atoms.

Also included are the enantiomers of each racemate.

A preferred compound is [2,3-dichloro-4-(6ethyl-3-oxo-1-cyclohexen-1-yl)phenoxy]acetic acid, its pure racemate, its pure (+) and (−)-enantiomers and their salts.

Also preferrred is [2,3-dichloro-4-(3-oxo-1cyclohexen-1-yl)phenoxy]acetic acid.

Also preferrred is [2,3-dichloro-4-(6-methyl-3-oxo-1-cyclohexen-1-yl)phenoxy]acetic acid.

Also preferrred is [2,3-dichloro-4-(4-methyl-3-oxo-1-cyclohexen-1-yl)phenoxy]acetic acid.

Also preferrred is [2,3-dichloro-4-(5-methyl-3-oxo-1-cyclohexen-1-yl)phenoxy]acetic acid, its pure (+) and (−) enantiomers and their salts.

Also preferrred is [2,3-dichloro-4-(2-methyl-3-oxo-1-cyclohexen-1-yl)phenoxy]acetic acid.

Also preferrred is [2,3-dichloro-4-(4,5-dimethyl-3-oxo-1-cyclohexen-1-yl)phenoxy]acetic acid.

Also preferrred is [2,3-dichloro-4-(5,5-dimethyl-3-oxo-1-cyclohexen-1-yl)phenoxy]acetic acid.

Also preferrred is ethyl [2,3-dichloro-4-(6-ethyl-3-oxo-1-cyclohexen-1-yl)phenoxy]acetate.

Also preferrred is [2,3-dichloro-4-(2,5-dimethyl-3-oxo-1-cyclohexen-1-yl)phenoxy]acetic acid.

Also preferrred is [3-chloro-4-(6-ethyl-3-oxo-1-cyclohexen-1-yl)phenoxy]acetic acid.

Also preferrred is [2,3-dichloro-4-(5-ethyl-3-oxo-1-cyclohexen-1-yl)phenoxy]acetic acid.

Also preferrred is [2,3-dichloro-4-(6-ethyl-4-methyl-3-oxo-1-cyclohexen-1-yl)phenoxy]acetic acid.

Also preferrred is [2,3-dichloro-4-(6-ethyl-5-methyl-3-oxo-1-cyclohexen-1-yl)phenoxy]acetic acid.

Also preferrred is 4-[2,3-dichloro-4-(6-ethyl-3-oxo-1-cyclohexen-1-yl)phenoxy]buturic acid.

Also preferrred is [2,3-dichloro-4-(6-cyclo-pentyl-3-oxo-1-cyclohexen-1-yl)phenoxy]acetic acid.

Also preferrred is [2,3-dichloro-4-(5-phenyl-3-oxo-1-cyclohexen-1-yl)phenoxy]acetic acid.

Also preferrred is [2,3-dichloro-4-(5-(2fluorophenyl)-3-oxo-1-cyclohexen-1-yl)phenoxy]acetic acid.

Also preferrred is 1-carboxy-1-methylethyl [2,3-dichloro-4-(6-ethyl-3-oxo-1-cyclohexen-1-yl)phenoxy]acetate.

Also preferrred is ethyl [2,3-dichloro-4-(5methyl-3-oxo-1-cyclohexen-1-yl)phenoxy]acetate.

Also preferrred is 1-carboxy-1-methylethyl [2,3-dichloro-4-(5-methyl-3-oxo-1-cyclohexen-1-yl)phenoxy]acetate.

Also preferrred is [2,3-dichloro-(6-ethyl-3(hydroximino)-1-cyclohexen-1-yl)phenoxy]acetic acid.

Especially preferred are the pure enantiomers since, in most instances, one enantiomer is more active biologically then its antipode.

Included within the scope of this invention are the pharmaceutically acceptable salts of substituted [2,3-dihydro-4-(3-oxo-1-cyclohexen-1-yl)phenoxy]alkanoic acids, since a major medical use of these compounds is solutions of their soluble salts which can be administered parenterally.

Thus, the acid addition salts can be prepared by the reaction of the substituted [2,3-dihydro-4-(3-oxo-1-cyclohexen-1-yl)phenoxy]alkanoic acids of this invention with an appropriate amine, ammonium hyrdoxide, guanidine, alkali metal hydroxide, alkali metal carbonate, alkali metal bicarbonate, quaternary ammonium hydroxide and the like. The salts selected are derived from among the non-toxic, pharmaceutically acceptable bases.

The synthesis of the substituted [2,3-dihydro-4-(3-oxo-1-cyclohexen-1-yl)phenoxy]alkanoic acids of formula I are generally carried out by the following route. The starting materials (formula III) and alkyl acetoacetate (formula IV) are refluxed in the presence of sodium methoxide or sodium ethoxide in ethanol. Intermediates are formed (formula V) but are not isolated. After evaporation of the alcohol and treatment with water, the intermediates undergo acid hydrolysis which causes loss of carbon dioxide to give the substituted [2,3-dihydro-4-(3-oxo-1-cyclohexen-1-yl)phenoxy[alkanoic acids of the present invention (formula Ia). The starting materials used in these Examples are obtained as shown in U.S. Pat. No. 3,255,241.

This synthetic route is illustrated below:

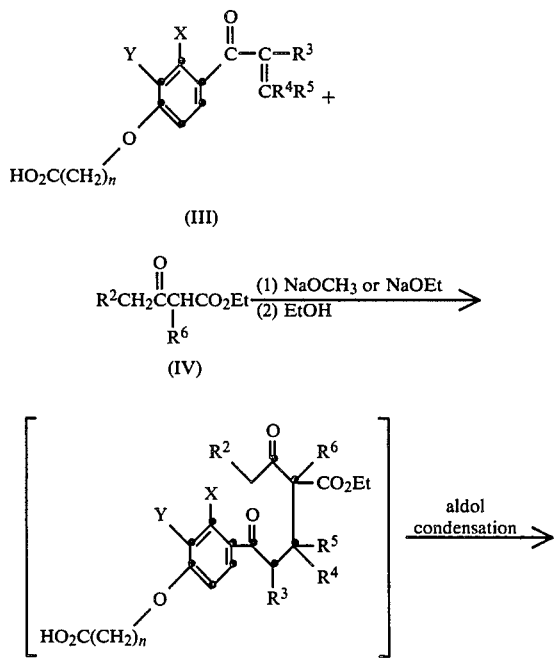

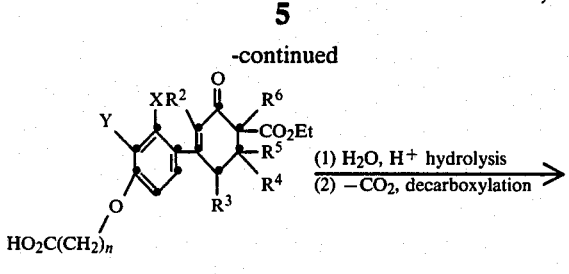

(V)

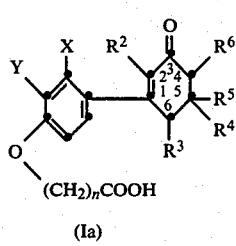

(Ia)

Those compounds possessing an asymmetric carbon atom at positions 4, 5 or 6 of the cyclohexene ring consist of a racemate composed of two enantiomers. Compounds bearing two different substituents at positions 4- and 5-, 4- and 6-, or 5- and 6- can give rise to two diasteriomers. (See the cyclohexene ring numbering system illustrated by the numbers inside the ring of structure Ia.) The two diasteriomers can be separated by chromatography. The resolution of each racemate may be accomplished by forming a salt of the racemic mixture with an optically active base such as (+) or (−)amphetamine, (−)cinchonidine, dehydroabietylamine, (+) or (−)-α-methylbenzylamine, (+) or (−)(1-naphthyl)ethylamine (+) cinchonine, brucine, or strychnine and the like in a suitable solvent such as methanol, ethanol, 2-propanol, benzene, acetonitrile, nitromethane, acetone and the like. There is formed in the solution, two diastereomeric salts, one of which is usually less soluble in the solvent than the other. Repetitive recrystallization of the crystalline salt generally affords a pure diastereomeric salt from which is obtained the desired pure enantiomer. The optically pure enantiomer of the compound of Formula I is obtained by acidification of the salt with a mineral acid, isolation by filtration and recrystallization of the optically pure antipode.

The other optically pure antipode may generally be obtained by using a different optically active base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

The salts are prepared by reacting the acids of Formula I with an appropriate base, for example, alkali metal or alkaline earth bicarbonate, carbonate or alkoxide, an amine, ammonia, an organic quaternary ammonium hydroxide, guanidine and the like.

The reaction is generally conducted in water when alkali metal hydroxides are used, but when alkoxides and the organic bases are used, the reaction may be conducted in an organic solvent, such as ether, ethanol, dimethylformamide and the like.

The preferred salts are the pharmaceutically acceptable salts such as sodium, potassium, ammonium and the like.

Inasmuch as there are a variety of symptoms and severity of symptoms associated with grey matter edema, particularly when it is caused by head trauma, stroke, cerebral hemorrhage or embolism, post-operative brain surgery trauma, spinal cord injury, cerebral infections and various brain concussions, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evaluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 50 mg/kg of body weight as a single dose, preferably from 0.5 mg/kg to 20 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, 3 intravenous doses of 8, 12 and 16 mg/kg of body weight can be given at 6 hour intervals. If necessary, 4 additional doses of 16 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an antiinflammatory steroid. These steroids are of some, albeit limited, use in control of white matter edema associated with ischemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as water, saline or dextrose solution by forming a soluble salt in water using an appropriate base, such as a pharmaceutically acceptable alkali metal hydroxide, alkali metal bicarbonate, ammonia, amine or guanidine. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, antioxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. Aug. 29-31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial as a secondary, inhibitable process. At the molecular level, the sequence appears to be: trauma, elevation of extracellular $K^{30}$ and/or release of neurotransmitters, edema, hypoxia and necrosis. Astroglial swelling results directly from a $K^{30}$-dependent, cation-coupled, chloride transport from the extracellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H, K,. Eds.; Raven Press: New York, 1979; p. 347, by Bourke, R. S.; Kimelberg, H, K.; Daze, M. A. in Brain Res. 1978, 154, 196, and by Bourke, R. S.; Kimelberg, H. K,; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, C.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V.; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention exhibited marked activity. This test provided the principal in vitro evaluation and consisted of a determination of concentration vs. response curve. The addition of $HCO_3^-$ to isotonic, $K^+$-rich saline-glucose incubation media is known to specifically stimulate the transport of Cl⁻ coupled with Na⁺ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulated statistically significant and comparable increases in cerebrocortical tissue swelling and ion levels. After addition of drug to the incubation media, detailed drug concentration-response curves were then obtained. The data were expressed as percent $HCO_3^-$-stimulated swelling vs. drug concentration, from which the concentration of drug providing 50% inhibition of $HCO_3^-$-stimulated swelling ($I_{50}$ in molarity) was interpolated. The results are expressed in Table I, below:

TABLE I

| Example | R¹ | n | Y | X | R² | Z | R³ | R⁴ | R⁵ | R⁶ | Entio-mer | $I_{50}$ (M) |
|---|---|---|---|---|---|---|---|---|---|---|---|---|
| 2 | H | 1 | Cl | Cl | H | O | H | H | H | H | ± | $10^{-8}$ |
| 3 | H | 1 | Cl | Cl | H | O | $CH_3$ | H | H | H | ± | $2 \times 10^{-7}$ |
| 4 | H | 1 | Cl | Cl | H | O | H | H | H | $CH_3$ | ± | $10^{-8}$ |
| 5 | H | 1 | Cl | Cl | H | O | H | $CH_3$ | H | H | ± | $10^{-8}$ |
| 6 | H | 1 | Cl | Cl | $CH_3$ | O | H | H | H | H | ± | $10^{-7}$ |
| 7 | H | 1 | Cl | Cl | H | O | H | $CH_3$ | H | $CH_3$ | ± | $10^{-8}$ |
| 8 | H | 1 | Cl | Cl | H | O | H | $CH_3$ | $CH_3$ | H | ± | $5 \times 10^{-7}$ |
| 9 | H | 1 | Cl | Cl | $CH_3$ | O | H | $CH_3$ | H | H | ± | $10^{-7}$ |
| 10 | H | 1 | Cl | Cl | H | O | H | $C_2H_5$ | H | H | ± | $8 \times 10^{-8}$ |
| 11 | H | 1 | Cl | Cl | H | O | $C_2H_5$ | H | H | H | ± | $>10^{-5}$ |
| 12 | H | 1 | Cl | Cl | H | O | $C_2H_5$ | H | H | H | + | $>10^{-6}$ |
| 13 | H | 1 | Cl | Cl | H | O | $C_2H_5$ | H | H | H | − | $>10^{-6}$ |
| 14 | $C_2H_5$ | 1 | Cl | Cl | H | O | $C_2H_5$ | H | H | H | ± | $10^{-10}$ |
| 15 | $C(CH_3)_2COOH$ | 1 | Cl | Cl | H | O | $C_2H_5$ | H | H | H | ± | $5 \times 10^{-7}$ |
| 16 | H | 1 | Cl | Cl | H | NOH | $C_2H_5$ | H | H | H | ± | $7 \times 10^{-8}$ |
| 17 | H | 3 | Cl | Cl | H | O | $C_2H_5$ | H | H | H | ± | $>10^{-6}$ |
| 18 | H | 1 | H | Cl | H | O | $C_2H_5$ | H | H | H | ± | $2 \times 10^{-7}$ |
| 19 | H | 1 | Cl | Cl | H | O | $C_2H_5$ | H | H | $CH_3$ | ± | $9 \times 10^{-9}$ |
| 20 | H | 1 | Cl | Cl | H | O | $C_2H_5$ | H | $CH_3$ | H | ± | $10^{-6}$ |
| 21 | H | 1 | Cl | Cl | H | O | $(CH_2)_2CH_3$ | H | H | H | ± | $>10^{-6}$ |
| 22 | H | 1 | Cl | Cl | H | O | cyclopropyl | H | H | H | ± | $>10^{-5}$ |
| 23 | H | 1 | Cl | Cl | H | O | H | phenyl | H | H | ± | $2 \times 10^{-7}$ |
| 24 | H | 1 | Cl | Cl | H | O | H | 4-F-phenyl | H | H | ± | $>10^{-6}$ |
| 25 | H | 1 | Cl | Cl | H | O | H | 2-F-phenyl | $CH_3$ | H | ± | $10^{-7}$ |
| 26 | H | 1 | Cl | Cl | H | O | H | H | $CH_3$ | H | + | NT |
| 27 | H | 1 | Cl | Cl | H | O | H | H | $CH_3$ | H | − | NT |
| 28 | $C_2H_5$ | 1 | Cl | Cl | H | O | H | H | $CH_3$ | H | ± | NT |
| 29 | $C(CH_3)_2COOH$ | 1 | Cl | Cl | H | O | H | H | $CH_3$ | H | ± | NT |

NT = not tested

It is to be noted that although some of the carboxylic acids of Formula I, such as the compounds of Example 11, possess modest in vitro cerebrocortical tissue slice activity, certain of their derivatives, such as their esters (Examples 14 and 15) or their oximes (Example 16) possess potent activity.

Thus, in the in vitro assay compounds of Formula I inhibit chloride transport by 50% at concentrations as low as $10^{-10}$ molar.

The following Examples are included to illustrate the in vitro cerebrocortical tissue slice assay, the preparation of representative compounds of Formula I and representative dosage forms of these compounds. It is intended that the specification and Examples be considered as exemplary only, with the true scope and spirit of the invention being indicated by the following claims.

In Examples 2, 4 and 6 and any other compound where $R^3=R^4=R^5=H$, the required precursor of compounds of Formula III (IIIa) is generated in situ from [2,3-dichloro-4-[3-(dimethylamino-1-oxo-propyl)-phenoxy]acetic acid (VI).

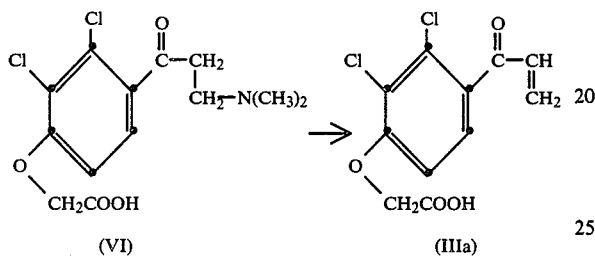

EXAMPLE 1

In Vitro Cerebrocortical Tissue Slice Assay

Adult cats of 2–3 kg body weight were employed in tissue slice studies. Prior to sacrifice, the animals were anesthetized with ketamine hydrochloride (Ketaset), 10 mg/kg im. Eight (three control, five experimental) pial surface cerebrocortical tissue slices (0.5-mm thick; approximately 150 mg initial fresh weight) were cut successively with a calibrated Stadie-Riggs fresh tissue microtome without moistening and weighed successively on a torsion balance. During the slice preparation all operations except weighing were confined to a humid chamber. Each slice was rapidly placed in an individual Warburg flask containing 2 ml of incubation medium at room temperature. The basic composition of the incubation media, in millimoles per liter, was as follows: glucose, 10; $CaCl_2$, 1.3; $MgSO_4$, 1.2; $KHSO_4$, 1.2; Hepes (N-2-hydroxyethylpiperazine-N'-2-ethane-sulfonic acid, titrated with NaOH to pH 7.4), 20. Except when adding $HCO_3^-$, the osmolarity of the media was maintained isosmotic (approximately 285 mOsm/L) by reciprocal changes of $Na^+$ or $K^+$ to achieve a concentration of $K^+$ of 27 mM. The basic medium was bubbled for 30 minutes with 100% $O_2$ before use. When added, $NaHCO_3$ or triethylammonium bicarbonate (TEAB) was initially present in the sidearm of each flask at an initial concentration of 50 mM in 0.5 ml of complete medium. Nonbicarbonate control slices were incubated at 37° C. in 2.5 ml of basic medium for 60 minutes. Bicarbonate control slices were similarly incubated for an initial 20 minutes at 37° C. in 2.0 ml of basic medium to which was added from the sidearm an additional 0.5 ml of incubation medium containing 50 mM $HCO_3^-$, which, after mixing, resulted in a $HCO_3^-$ concentration of 10 mM and a total volume of 2.5 ml. The incubation continued for an additional 40 minutes. The various compounds tested were dissolved by forming the sodium salts by treatment with a molar equivalent of $NaHCO_3$ and diluting to the appropriate concentrations. Just prior to incubation, all flasks containing $HCO_3^-$ were gassed for 5 minutes with 2.5% $CO_2$/97.5% $O_2$ instead of 100% $O_2$.

Following the 60-minute incubation period, tissue slices were separated from incubation medium by filtration, reweighed, and homogenized in 1 N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration was measured by the amount of $HCO_3^-$-stimulated swelling that occurred in its presence, computed as a percent of the maximum possible. Tissue and media $Na^{30}$ and $K^+$ were determined by emission flame photometry with $Li^+$ internal standard; $Cl^-$ was determined by amperometric titration. Tissue viability during incubation was monitored by manometry.

EXAMPLE 2

Preparation of [2,3-dichloro-4-(3-oxo-1-cyclohexen-1-yl)phenoxy]acetic acid

Step A:
[2,3-Dichloro-4-(3-dimethylaminopropvl)-phenoxy]acetic acid hydrochloride (2,3-Dichloro-4-acetylphenoxy)acetic acid (U.S. Pat. No. 3,453,312) (7.89 g, 0.03 mole), dimethylamine hydrochloride (2.34 g, 0.03 mole), paraformaldehyde (1.05 g, 0.033 mol. equiv.) and glacial acetic acid (1 ml) were combined and heated on a steam bath for two hours. The reaction mixture was treated with hot ethanol (50 ml) and then cooled. The white solid was separated by filtration, washed with ethanol, dried and recrystallized from a mixture of ethanol and ether to give [2,3-dichloro-4-(3-dimethylaminopropyl)phenoxy]acetic acid hydrochloride, m.p. 194°–196° C.

Elemental Analysis for $C_{13}H_{15}Cl_2NO_4 \cdot HCl$
Calc'd: C, 43.78; H, 4.52; N, 3.93%.
Found: C, 43.91; H, 4.57; N, 3.71%.

Step B:
[2,3-Dichloro-4-(3-oxo-1-cyclohexen-1-yl)-phenoxy]acetic acid

To a stirred solution of sodium methoxide (0.5 g, 0.009 moles) in ethanol (40 ml) and ethyl acetoacetate (0.9 ml) was added [2,3-dichloro-4-(3-dimethylamino-1-oxopropyl)phenoxy]acetic acid (0.95 g, 0.0027 mole). The reaction mixture was heated at reflux for 2½ hours then the solvent was distilled at reduced pressure. The residue was dissolved in water, acidified with hydrochloric acid, extracted with ether, washed with water, dried over magnesium sulfate and evaporated at reduced pressure to give 50 mg of [2,3-dichloro-4-(3-oxo-1-cyclohexen-1-yl)phenoxy]acetic acid which melted at 197°–198° C. after purification by thin layer chromatography on silica gel ($CH_2Cl_2$:THF:methanol; 50:1:1).

Elemental Analysis for $C_{14}H_{12}Cl_2O_4$ Calc'd: C, 53.35; H, 3.84. Found: C, 53.65; H, 3.96.

EXAMPLE 3

Preparation of [2,3-dichloro-4-(6-methyl-3-oxo-1-cyclohexen-1-yl)phenoxy]acetic acid To a stirred solution of sodium methoxide (2.0 g, 0.037 mole) in ethanol (60 ml) and ethyl acetoacetate (4.86 ml) was added [2,3-dichloro-4-(2-methylene-1- oxopropyl)phenoxy]acetic acid (4.8 g, 0.017 mole). The reaction mixture was heated at reflux for 3 hours then the solvent was distilled at reduced pressure. The residue was dissolved in water, acidified with hydrochloric acid, extracted with ether, washed with water, extracted in sodium bicarbonate and acidified to get a precipitate which was filtered, rinsed with water, dried, and recrystallized from 500 ml toluene to give 2,3-dichloro-4-(6-methyl-3-oxo-1-cyclohexen-1-yl)phenoxy]acetic acid which melted at 185° C.

Elemental Analysis for $C_{15}H_{14}Cl_2O_4$ Calc'd: C, 54.73; H, 4.29. Found: C, 54.86; H, 4.25.

EXAMPLE 4

Preparation of [2,3-dichloro-4-(4-methyl-3-oxo-1-cyclohexen-1-yl)phenoxy]acetic acid To a stirred solution of sodium methoxide (3.5 g, 0.065 mole) in ethanol (100 ml) and ethyl-2-methylacetoacetate (6.6 ml) was added [2,3-dichloro-4-(3-dimethylamino-1-oxopropyl)phenoxy]acetic acid hydrochloride (7.4 g, 0.021 mole). The reaction mixture was heated at reflux for 3 hours then the solvent was distilled at reduced pressure, treated with 100 ml of 2% sodium hydroxide, heated on a steam bath for 1½ hours, then acidified, extracted with ether, washed with water, dried over magnesium sulfate and evaporated at reduced pressure. The residue was triturated with 100 ml of hot toluene, filtered, and dried to give 0.9 of [2,3-dichloro-4-(4-methyl-3-oxo-1-cyclohexen-1-yl)phenoxy]acetic acid which melted at 183°–185° C. after recrystallization from 30 ml of toluene.

Elemental Analysis for $C_{15}H_{14}Cl_2O_4$ Calc'd: C, 54.73; H, 4.29. Found: C, 54.77; H, 4.22.

EXAMPLE 5

Preparation of [2,3-dichloro-4-(5-methyl-3-oxo-1-cyclohexen-1-yl)phenoxy]acetic acid To a stirred solution of sodium (0.836 g, 0.0363 mole) in ethanol (70 ml) and ethyl acetoacetate (4.73 g, 0.0363 mole) was added [2,3-dichloro-4-(1-oxo-2-butenyl)-phenoxy]acetic acid (4.67 g, 0.0162 mole). The reaction mixture was heated at reflux for 3 hours then the solvent was distilled at reduced pressure. The residue was dissolved in water, acidified with hydrochloric acid, extracted with ether, washed with water, dried over magnesium sulfate and evaporated at reduced pressure to give 3.7 g of [2,3-dichloro-4-(5-methyl-3-oxo-1-cyclohexen-1-yl)phenoxy]acetic acid which melted at 187°–190° C. after recrystallization from acetonitrile.

Elemental Analysis for $C_{15}H_{14}Cl_2O_4$ Calc'd: C, 54.73; H, 4.29. Found: C, 55.08; H, 4.41.

EXAMPLE 6

Preparation of [2,3-dichloro-4-(2-methyl-3-oxo-1-cyclohexen-1-yl)phenoxy]acetic acid To a stirred solution of sodium methoxide (7.2 g, 0.133 mole) in ethanol (240 ml) and ethyl 3-oxopentanoate (13.5 ml) was added [2,3-dichloro-4-(3-dimethylamino-1-oxopropyl)phenoxy]acetic acid hydrochloride (15.0 g, 0.042 mole). The reaction mixture was heated at reflux for 3 hours, the solvent was distilled at reduced pressure, then the mixture was treated with 150 ml of 2.5% sodium hydroxide and heated on a steam bath for 2½ hours. The mixture was diluted with water, acidified, extracted into ether, washed with water, brine, dried over magnesium sulfate and evaporated at reduced pressure to give 4.1 g of [2,3-dichloro-4-(2-methyl-3-oxo-1-cyclohexen-1-yl)phenoxy]acetic acid which melted at 143°–145° C. after recrystallization from butyl chloride.

Elemental Analysis for $C_{15}H_{14}Cl_2O_4$ Calc'd: C, 54.73; H, 4.29. Found: C, 54.50; H, 4.24.

EXAMPLE 7

Preparation of [2,3-dichloro-4-(4,5-dimethyl-3-oxo-1-cyclohexen-1-yl)phenoxy]acetic acid To a stirred solution of sodium (0.967 g, 0.042 mole) in ethanol (95 ml) and ethyl 3-oxo-2-methylbutanoate (6.06 g, 0.042 mole) was added [2,3-dichloro-4-(1-oxo-2-butenyl)phenoxy]acetic acid (5.4 g, 0.0187 mole). The reaction mixture was heated at reflux for 3 hours, 50 ml water and 20 ml 1N sodium hydroxide was added, and reflux was continued for 1 hour, then the solvent was distilled at reduced pressure. The residue was dissolved in water, acidified, extracted with ether, then extracted with methylene chloride. The combined extracts were washed with water, dried over magnesium sulfate and evaporated at reduced pressure to give 1.8 g of [2,3-dichloro-4-(4,5-dimethyl-3-oxo-1-cyclohexen-1-yl)phenoxy]acetic acid which melted at 151°–153° C. after recrystallization from 20 ml of methanol and 5 ml of hexane.

Elemental Analysis for $C_{16}H_{16}Cl_2O_4$ Calc'd: C, 55.99; H, 4.70. Found: C, 56.21; H, 4.82.

EXAMPLE 8

Preparation of [2,3-dichloro-4-(5,5-dimethyl-3-oxo-1-cyclohexen-1-yl)phenoxy]acetic acid To a stirred solution of sodium (1.449 g, 0.063 mole) in ethanol (150 ml) and ethyl acetoacetate (8.20 g, 0.063 mole) was added (2,3-dichloro-4-(3-methyl-1-oxo-2-butenyl)phenoxy]acetic acid (9.09 g, 0.03 mole). The reaction mixture was heated at reflux for 3½ hours then the solvent was distilled at reduced pressure. The residue was acidified with hydrochloric acid, extracted with ether and sodium bicarbonate, acidified with hydrochloric acid, extracted with ether and methylene chloride, washed with water, dried over magnesium sulfate, and evaporated at reduced pressure to give 4.5 g of [2,3-dichloro-4-(5,5-dimethyl-3-oxo-1-cyclohexen-1-yl)phenoxy]acetic acid which melted at 178°–180° C. after purification by chromatography on silica and recrystallization from 42 ml of acetonitrile.

Elemental Analysis for $C_{16}H_{16}Cl_2O_4$ Calc'd: C, 55.99; H, 4.70 Found: C, 56.34; H, 4.79

EXAMPLE 9

Preparation of [2,3-dichloro-4-(2,5-dimethyl-3-oxo-1-cyclohexen-1-yl)phenoxy]acetic acid To a stirred solution of sodium (1.39 g, 0.0604 mole) in ethanol (110 ml) and ethyl 3-oxo-pentanoate (8.71 g, 0.0604 mole) was added [2,3-dichloro-4-(1-oxo-2-butenyl)phenoxy]acetic acid (8.03 g, 0.028 mole). The reaction mixture was heated at reflux for 4 hours then the solvent was distilled at reduced pressure. 11N sodium hydroxide (125 ml) and 75 ml of water was added and refluxing was continued for 3 hours. The reaction mixture was cooled, acidified with hydrochloric acid, extracted with ether and methylene chloride, washed with brine, dried over magnesium sulfate and evaporated at reduced pressure to give 6.5 g of [2,3-dichloro-4-(2,5-dimethyl-3-oxo-1-cyclohexen-1-yl)phenoxy]acetic acid which melted at 170°–173° C. after recrystallization from 30 ml of acetonitrile.

Elemental Analysis for $C_{16}H_{16}Cl_2O_4$ Calc'd: C, 55.99; H, 4.70 Found: C, 56.32; H, 4.83

EXAMPLE 10

Preparation of [2,3-dichloro-4-(5-ethyl-3-oxo-1-cyclohexen-1-yl)phenoxy]acetic acid To a stirred solution of sodium (0.6577 g, 0.0286 mole) in ethanol (100 ml) and ethyl acetoacetate (3.72 g, 0.0286 mole) was added [2,3-dichloro-4-(1-oxo-2-pentenyl)phenoxy]acetic acid (3.6 g, 0.01187 mole). The reaction mixture was heated at reflux for 4 hours then the solvent was distilled at reduced pressure. The residue was refluxed in 100 ml 1N sodium hydroxide and 100 ml water for 1½ hours, acidified with hydrochloric acid, extracted with ether, washed with water, dried over magnesium sulfate and evaporated at reduced pressure to give [2,3-dichloro-4-(5-ethyl-3-oxo-1-cyclohexen-1-yl)phenoxy]acetic acid which melted at 163°–165° C. after purification by chromatography on silica gel and recrystallization from 22 ml of acetonitrile.

Elemental Analysis for $C_{16}H_{16}Cl_2O_4$ Calc'd: C, 55.99; H, 4.70 Found: C, 56.14; H, 4.81

EXAMPLE 11

Preparation of [2,3-dichloro-4-(6-ethyl-3-oxo-1-cyclohexen-1-yl)phenoxy]acetic acid To a stirred solution of sodium methoxide (24.3 g, 0.45 mole) in ethanol (700 ml) and ethyl acetoacetate (58.6 g, 0.45 mole) was added [2,3-dichloro-4-(2-methylene-1-oxobutyl)phenoxy]acetic acid (60.6 g, 0.20 mole). The reaction mixture was heated at reflux for 2½ hours, then the solvent was distilled at reduced pressure. The residue was dissolved in water, acidified with hydrochloric acid, extracted into ether, washed with water, extracted into sodium bicarbonate, acidified, extracted into ether, dried over magnesium sulfate, filtered and evaporated in vacuo to give 68 g of [2,3-dichloro-4-(6-ethyl-3-oxo-1-cyclohexen-1-yl)phenoxy]acetic acid which melts at 170°–172° after recrystallization from nitromethane.

Elemental Analysis for $C_{16}H_{16}Cl_2O_4$ Calc'd: C, 55.99; H, 4.70 Found: C, 55.66; H, 4.84

EXAMPLE 12

Preparation of (+)[2,3-dichloro-4-(6-ethyl-3-oxo-1-cyclohexen-1-yl)phenoxy]acetic acid A mixture of [2,3-dichloro-4-(6-ethyl-3-oxo-1-cyclohexen-1-yl)-phenoxy]acetic acid (13.7 g, 0.04 mole), (+)-α-methylbenzylamine (5.12 ml, 0.04 mole) and 2-propanol (100 ml) were heated to boiling, filtered and cooled. The salt which separated was recrystallized four times from 2-propanol. The recrystallized salt was suspended in water, hydrochloric acid and ether. The ether extract was washed with water, dried over magnesium sulfate and evaporated in vacuo to give 0.55 g of the (+) enantiomer of [2,3-dichloro-4-(6-ethyl-3-oxo-1-cyclohexen-1-yl)phenoxy]acetic acid which melts at 164°–165° C. after recrystallization from butyl chloride.

Elemental Analysis for $C_{16}H_{16}Cl_2O_4$ Calc'd: C, 55.99; H, 4.70 Found: C, 56.07; H, 4.72 $[\alpha]_D^{25} = +208°$ (Cl, acetone)

EXAMPLE 13

Preparation of (−)[2,3-dichloro-4-(6-ethyl-3-oxo-1-cyclohexen-1-yl)phenoxy]acetic acid By following the procedure described in Example 12, but substituting for the (+)-α-methylbenzylamine therein described an equal amount of (−)-α-methylbenzylamine there is obtained 200 mg of the (−)-enantiomer of [2,3-dichloro-4-(6-ethyl-3-oxo-1-cyclohexen-1-yl)phenoxy]acetic acid which melts at 165°–167° C.

Elemental Analysis for $C_{16}H_{16}Cl_2O_4$ Calc'd: C, 55.99; H, 4.70 Found: C, 56.07; H, 4.75

EXAMPLE 14

Preparation of ethyl [2,3-dichloro-4-(6-ethyl-3-oxo-1-cyclohexen-1-yl)phenoxy]acetate A stirred solution of [2,3-dichloro-4-(6-ethyl-3-oxo-1-cyclohexen-1-yl)phenoxy]acetic acid (3.43 g, 0.01 mole) in ethanol (50 ml) containing sulfuric acid (4 drops) was heated at reflux for 4 hours. The ethanol was evaporated at reduced pressure, the residue dissolved in ether, washed with dilute sodium hydroxide, water, dried over magnesium sulfate and evaporated in vacuo to give 3.31 g of ethyl [2,3-dichloro-4-(6-ethyl-3-oxo-1-cyclohexen-1-yl)-phenoxy]acetate which melted at 110°–112° C.

Elemental Analysis for $C_{18}H_{20}Cl_2O_4$ Calc'd: C, 58.23; H, 5.43 Found: C, 58.43; H, 5.62

EXAMPLE 15

Preparation of 1-carboxy-1-methylethyl [2,3-dichloro-4-(6-ethyl-3-oxo-1-cyclohexen-1-yl)phenoxy]acetate To a stirred solution of [2,3-dichloro-4-(6-ethyl-3-oxo-1-cyclohexen-1-yl)phenoxy]acetic acid (2.06 g, 0.006 mole) under nitrogen in tetrahydrofuran (THF) (50 ml) was added 1,1'-carbonyldiimidazole (0.97 g, 0.006 mole). The solution was stirred for 1 hour then 2-hydroxy-2-methylpropanoic acid (0.62 g, 0.006 mole) in THF (25 ml) was added and stirring was continued overnight. The THF was evaporated in vacuo and the residue chromatographed on silica (300 g) eluting with $CH_2Cl_2$-THF-AcOH (100:2:1). Evaporation of the pertinent fractions gave 1-carboxy-1-methylethyl [2,3-dichloro-4-(6-ethyl-3-oxo-1-cyclohexen-1-yl)phenoxy-]acetate which melted at 167°–168° C.

Elemental Analysis for $C_{20}H_{21}Cl_2O_6$ Calc'd: C, 56.08; H, 4.94 Found: C, 56.42; H, 5.37

EXAMPLE 16

Preparation of [2,3-dichloro-4-(6-ethyl-3-(hydroxyimino)-1-cyclohexen-1-yl)phenoxy]acetic acid hemitoluene solvate A mixture of [2,3-dichloro-4-(6-ethyl-3-oxo-1-cyclohexen-1-yl)phenoxy]acetic acid (3.4 g, 0.01 mole), hydroxylamine hydrochloride (2.1 g, 0.03 mole) and pyridine (40 ml) were heated at 95° C. for 40 hours, poured into ice-water and hydrochloric acid, extracted with ether, washed with water, dried over magnesium sulfate and evaporated in vacuo. After recrystallization from toluene (120 ml) the [2,3-dichloro-4-(6-ethyl-3-(hydroxyimino)-1-cyclohexen-1-yl)-phenoxy]acetic acid hemitoluene solvate melted at 88°–90° C.

Elemental Analysis for $C_{16}H_{17}Cl_2NO_4.\frac{1}{2}C_7H_8$ Calc'd: C, 57.93; H, 5.24; N, 3.46 Found: C, 57.72; H, 5.22; N, 3.38

EXAMPLE 17

Preparation of 4-[2,3-dichloro-4-(6-ethyl-3-oxo-1-cyclohexen-1-yl)phenoxy]butyric acid To a stirred solution of sodium methoxide (2.4 g, 0.044 mole) in ethanol (100 ml) and ethyl acetoacetate (5.9 ml) was added 4-[2,3-dichloro-4-(2-methylene-1-oxobutyl)phenoxy]butyric acid (6.6 g, 0.02 mole). The reaction mixture was heated at reflux for 2½ hours then the solvent was distilled at reduced pressure. The residue was dissolved in water, acidified with hydrochloric acid, extracted into ether, washed with water, extracted into sodium bicarbonate, acidified, extracted into ether, dried over magnesium sulfate, filtered and evaporated in vacuo to give 1.28 g of [2,3-dichloro-4-(6-ethyl-3-oxo-1-cyclohexen-1-yl)phenoxy]butyric acid which melted at 160°–162° C. after two recrystallizations from toluene and recrystallization from 300 ml butyl chloride.

Elemental Analysis for $C_{18}H_{20}Cl_2O_4$ Calc'd: C, 58.23; H, 5.43 Found: c, 58.54; H, 5.66

EXAMPLE 18

Preparation of [3-chloro-4-(6-ethyl-3-oxo-1-cyclohexen-1-yl)phenoxy]acetic acid

To a stirred solution of sodium (0.95 g, 0.0414 mole) in ethanol (75 ml) and ethyl acetoacetate (5.38 g, 0.0414 mole) was added [3-chloro-4-(2-methylene-1-oxobutyl)phenoxy]acetic acid (4.94 g, 0.0184 mole). The reaction mixture was heated at reflux for 3 hours. 1N sodium hydroxide (10 ml) and 55 ml of water was added and refluxing was continued for 1½ hours, then the solvent was distilled at reduced pressure. The residue was acidified, extracted with ether, washed with water, dried over magnesium sulfate to give 4.1 g of [3-chloro-4-(6-ethyl-3-oxo-1-cyclohexen-1-yl)phenoxy]acetic acid which melted at 138°–140° C. after recrystallization from butyl chloride and methanol.

Elemental Analysis for $C_{16}H_{17}ClO_4$ Calc'd: C, 62.24; H, 5.55 Found: c, 62.00; H, 5.50

EXAMPLE 19

Preparation of [2,3-dichloro-4-(6-ethyl-4-methyl-3-oxo-1-cyclohexen-1-yl)phenoxy]acetic acid To a stirred solution of sodium methoxide (2.4 g, 0.044 mole) in ethanol (80 ml) and ethyl 2-methyl-3-oxobutyrate (6.5 ml) was added [2,3-dichloro-4-(2-methylene-1-oxobutyl)phenoxy]acetic acid (6.06 g, 0.02 mole). The reaction mixture was heated at reflux for 2 hours, then the solvent was distilled at reduced pressure. The residue was dissolved in water, acidified with hydrochloric acid, extracted into ether, washed with water, extracted into sodium bicarbonate, acidified with hydrochloric acid, extracted into ether, washed with water, dried over magnesium sulfate and evaporated at reduced pressure to give [2,3-dichloro-4-(6-ethyl-4-methyl-3-oxo-1-cyclohexen-1-yl)phenoxy]acetic acid which melted at 99°–100° C. after purification by recrystallization from butyl chloride.

Elemental Analysis for $C_{17}H_{18}Cl_2O_4$ Calc'd: C, 57.16; H, 5.08. Found: C, 57.39: H, 5.12.

EXAMPLE 20

Preparation of [2,3-dichloro-4-(6-ethyl-5-methyl-3-oxo-1-cyclohexen-1-yl)phenoxy]acetic acid To a stirred solution of sodium methoxide (4.86 g, 0.09 mole) in ethanol (350 ml) and ethyl acetoacetate (11.7 ml) was added [2,3-dichloro-4-(2-ethylidene-1-oxobutyl)phenoxy]acetic acid (12.68 g, 0.04 mole). The reaction mixture was heated at reflux for 4½ hours, then the solvent was distilled at reduced pressure. The residue was dissolved in water, acidified, extracted with ether, washed with water, dried over magnesium sulfate and evaporated at reduced pressure to give [2,3-dichloro-(4-(6-ethyl-5-methyl-3-oxo-1-cyclohexen-1-yl)phenoxy]acetic acid which melted at 183° C. after recrystallization from 10 ml of butyl chloride and purification by chromatography (methylenechloride:THF:AcOH;50:1:1).

Elemental Analysis for $C_{17}H_{18}Cl_2O_4$ Calc'd: C, 57.16; H, 5.08. Found: C, 56.87; H, 5.04.

EXAMPLE 21

Preparation of [2,3-dichloro-4-(6-propyl-3-oxo-1-cyclohexen-1-yl)phenoxy]acetic acid To a stirred solution of sodium methoxide (2.0 g, 0.037 mole) in ethanol (70 ml) and ethyl acetoacetate (4.7 g) was added [2,3-dichloro-4-(2-methylene-1-oxopentyl)phenoxy]acetic acid (5.0 g, 0.016 mole). The reaction mixture was heated at reflux for 2½ hours then the solvent was distilled at reduced pressure. The residue was dissolved in water, acidified with hydrochloric acid, extracted into ether, washed with water, extracted into sodium bicarbonate, acidified, extracted into ether, washed with water, dried over magnesium sulfate and evaporated at reduced pressure to give 1.6 g of [2,3-dichloro-4-(6-propyl-3-oxo-1-cyclohexen-1-yl)phenoxy]acetic acid which melted at 177°–178° C. after recrystallization from toluene.

Elemental Analysis for $C_{17}H_{18}Cl_2O_4$ Calc'd: C, 57.16; H, 5.08. Found: C, 57.33; H, 5.17.

EXAMPLE 22

Preparation of [2,3-dichloro-4-(6-cyclopentyl-3-oxo-1-cyclohexen-1-yl)phenoxy]acetic acid To a stirred solution of sodium methoxide (2.3 g, 0.043 mole) in ethanol (50 ml) and ethyl acetoacetate (5.56 g, 0.043 mole) was added [2,3-dichloro-4-(2-methylene-2-cyclopentyl-1-oxoethyl)phenoxy]acetic acid (6.5 g, 0.019 mole). The reaction mixture was heated at reflux for 2 hours, then the solvent was distilled at reduced pressure. The residue was dissolved in water, acidified, extracted into ether, washed with water, extracted into sodium bicarbonate, acidified, extracted into ether, washed with water, dried over magnesium sulfate and evaporated under reduced pressure to give 2.6 g of [2,3-dichloro-4-(6-cyclopentyl-3-oxo-1-cyclohexen-1-yl)phenoxy]acetic acid which melted at 206°–207° C. after recrystallization from 300 ml of toluene.

Elemental Analysis for $C_{19}H_{20}Cl_2O_4$ Calc'd: C, 59.54; H, 5.26. Found: C, 59.24; H, 5.52.

EXAMPLE 23

Preparation of
[2,3-dichloro-4-(5-phenyl-3-oxo-1-cyclohexen-1-yl)phenoxy]acetic acid

Step A:
[2,3-Dichloro-4-(1-oxo-3-phenyl-2-propenyl)phenoxy]acetic acid

To a stirred suspension of [2,3-dichloro-4-(1-oxo-ethyl)phenoxy]acetic acid (15.78 g 0.06 mole) in 75 ml ethanol was added benzaldehyde (7.95 g, 0.075 mole) with stirring under nitrogen, followed by NaOH (8.0 g, 0.20 mole) in 16 ml of water. An additional 150 ml of ethanol was added and stirring was continued. The reaction mixture was heated at reflux for 1½ hours, poured into ice water and acidified with hydrochloric acid. The mixture was extracted with ethyl acetate and methylene chloride, washed with dilute hydrochloric acid, then brine, dried over magnesium sulfate and concentrated under reduced pressure to give 8.7 g of [2,3-dichloro-4-(1-oxo-3-phenyl-2-propenyl)phenoxy]acetic acid which melted at 190°-191° C. after recrystallization from acetonitrile.

Step B:
[2,3-Dichloro-4-(5-phenyl-3-oxo-1-cyclohexen-1-yl)phenoxy]acetic acid To a stirred solution of sodium (1.21 g, 0.0526 mole) in ethanol (150 ml) and ethyl acetoacetate (6.85 g, 0.0526 moles) was added [2,3-dichloro-4-(1-oxo-3-phenyl-2-propenyl)phenoxy]acetic acid (8.7 g, 0.0248 mole)(Step A). The reaction mixture was heated at reflux for 3 hours, then the solvent was distilled at reduced pressure. The residue was dissolved in water, extracted with ether, acidified with hydrochloric acid, extracted with methylene chloride and ethyl acetate, dried over magnesium sulfate and evaporated at reduced pressure to give [2,3-dichloro-4-(5-phenyl-3-oxo-1-cyclohexen-1-yl)phenoxy]acetic acid which melted at 197°-199° C.

Elemental Analysis for $C_{20}H_{16}Cl_2O_4$ Calc'd: C, 61.39; H, 4.12. Found: C, 61.66; H, 4.26.

EXAMPLE 24

Preparation of
[2,3-dichloro-4-(5-(4-fluorophenyl)-3-oxo-1-cyclohexen-1-yl)phenoxy]acetic acid

Step A:
[2,3-Dichloro-4-(3-(4-fluorophenyl-1-oxo-2-propenyl)-phenoxy]acetic acid To 300 ml of ethanol was added [2,3-dichloro-4-(1-oxo-ethyl)phenoxy]acetic acid (19.73 g, 0.075 mole), 4-fluorobenzaldehyde (13.63 g, 0.11 mole), sodium hydroxide (10 g) in 20 ml of water and 50 ml of ethanol with stirring under nitrogen. The reaction mixture was heated on a steam bath for 1¼ hours, cooled, and concentrated under reduced pressure. The residue was diluted with water, acidified with hydrochloric acid, stirred, filtered and washed with water to give 12.8 g of [2,3-dichloro-4-(3-(4-fluorophenyl)-1-oxo-2-propenyl)-phenoxy]acetic acid which melted at 194°-196° C. after purification by lixiviation with acetonitrile.

Step B:
[2,3-Dichloro-4-(5-(4-fluorophenyl)-3-oxo-1-cyclohexen-1-yl)phenoxy]acetic acid To a stirred solution of sodium (1.34 g, 0.0583 mole) in ethanol (150 ml) and ethyl acetoacetate (7.59 g, 0.0583 mole) was added [2,3-dichloro-4-(3-(4-fluorophenyl-1-oxo-2-propenyl)phenoxy]acetic acid (10.15 g, 0.0275 mole). The reaction mixture was heated at reflux for 3½ hours then the solvent was distilled at reduced pressure. The residue was dissolved in water, acidified with hydrochloric acid, extracted with ether, extracted with sodium bicarbonate, acidified, extracted with ether and methylene chloride, washed with water, dried over magnesium sulfate and evaporated at reduced pressure to give 7.5 g of [2,3-dichloro-4-(5-(4-fluorophenyl)-3-oxo-1-cyclohexen-1-yl)phenoxy]acetic acid which melted at 190°-192° C. after recrystallization from 75 ml of acetonitrile.

Elemental Analysis for $C_{20}H_{15}Cl_2FO_4$ Calc'd: C, 58.70; H, 3.69. Found: C, 58.89; H, 3.91.

EXAMPLE 25

Preparation of
[2,3-dichloro-4-(5-(2-fluorophenyl)-3-oxo-1-cyclohexen-1-yl)phenoxy]acetic acid

Step A:
[2,3-Dichloro-4-(3-(2-fluorophenyl)-1-oxo-2-propenyl)-phenoxy]acetic acid To 500 ml of ethanol was added [2,3-dichloro-4-(1-oxo-ethyl)phenoxy]acetic acid (19.73 g, 0.075 mole), 2-fluorobenzaldehyde (13.63 g, 0.11 mole), sodium hydroxide (10 g, 0.25 mole) in 20 ml of water and 50 ml of ethanol with stirring under nitrogen. The reaction mixture was refluxed for a total of 1½ hours. The reaction mixture was cooled, filtered, the gelatineous solid dispersed in water acidified with hydrochloric acid, stirred, filtered and washed with water. The residue was extracted with methylene chloride and ethyl acetate, washed with water, and concentrated under reduced pressure to give 15.2 g of [2,3-dichloro-4-(3-(2-fluorophenyl)-1-oxo-2-propenyl)phenoxy]acetic acid which melted at 191°-194° C. after purification.

Step B:
[2,3-Dichloro-4-(5-(2-fluorophenyl)-3-oxo-1-cyclohexen-1-yl)phenoxy]acetic acid To a stirred solution of sodium (1.449 g, 0.063 mole) in ethanol (150 ml) and ethyl acetoacetate (8.20 g, 0.063 mole) was added [2,3-dichloro-4-(3-(2-fluorophenyl-1-oxo-2-propenyl)phenoxy]acetic acid (11.07 g, 0.03 mole). The reaction mixture was heated at reflux for 3 hours then the solvent was distilled at reduced pressure. The residue was dissolved in ice water, extracted with ether, acidified with hydrochloric acid, extracted with methylene chloride, washed with water, dried over magnesium sulfate and evaporated at reduced pressure to give 4.6 g of [2,3-dichloro-4-(5-(2-fluorophenyl)-3-oxo-1-cyclohexen-1-yl)phenoxy]acetic acid which melted at 187°-190° C. after recrystallization from 50 ml of acetonitrile.

Elemental Analysis for $C_{20}H_{15}Cl_2FO_4$ Calc'd: C, 58.70; H, 3.69. Found: C, 58.85; H, 3.63.

EXAMPLE 26

Preparation of (+)[2,3-dichloro-4-(5-methyl-3-oxo-1-cyclohexen-1-yl)phenoxy]acetic acid By substituting an equimolar quantity of racemic [2,3-dichloro-4-(5-methyl-3-oxo-1-cyclohexen-1-yl)phenoxy]acetic acid (Example 5) for the racemic [2,3-dichloro-4-(6-ethyl-3-oxo-1-cyclohexen-1-yl)phenoxy]acetic acid used in Example 12, there is obtained (+)[2,3-dichloro-4-(5-methyl-3-oxo-1-cyclohexen-1-yl)acetic acid.

EXAMPLE 27

Preparation of (−)[2,3-dichloro-4-(5-methyl-3-oxo-1-cyclohexen-1-yl)phenoxy]acetic acid By substituting an equimolar quantity of racemic [2,3-dichloro-4-(5-methyl-3-oxo-1-cyclohexenyl)-phenoxy]acetic acid (Example 5) for the racemic [2,3-dichloro-4-(6-ethyl-3-oxo-1-cyclohexen-1-yl)phenoxy]acetic acid used in Example 13, there is obtained (−)[2,3-dichloro-4-(5-methyl-3-oxo-1-cyclohexen-1-yl)acetic acid.

EXAMPLE 28

Preparation of ethyl [2,3-dichloro-4-(5-methyl-3-oxo-cyclohexen-1-yl)phenoxy]acetate By substituting an equimolar quantity of 2,3-dichloro-4-(5-methyl-3-oxo-1-cyclohexen-1-yl)phenoxy]acetic acid for the [2,3-dichloro-4-(6-ethyl-3-oxo-1-cyclohexen-1-yl)phenoxy]acetic acid used in Example 14, there is obtained ethyl [2,3-dichloro-4-(5-methyl-3-oxo-1-cyclohexen-1-yl)acetate.

EXAMPLE 29

Preparation of 1-carboxy-1-methylethyl [2,3-dichloro-4-(5-methyl-3-oxo-1-cyclohexen-1-yl)phenoxy]acetate By substituting an equimolar quantity of [2,3-dichloro-4-(5-methyl-3-oxo-1-cyclohexen-1-yl)phenoxy]acetic acid for the [2,3-dichloro-4-(6-ethyl-3-oxo-1-cyclohexen-1-yl)phenoxy]acetic acid used in Example 15 and conducting the reaction as described in Example 15, there is obtained 1-carboxy-1-methylethyl [2,3-dichloro-4-(5-methyl-3-oxo-1-cyclohexen-1-yl)phenoxy]acetate.

EXAMPLE 30

Parenteral Solution of Sodium [2,3-dichloro-4-(5-methyl-3-oxo-1-cyclohexen-1-yl)phenoxy]acetate

[2,3-Dichloro-4-(5-methyl-3-oxo-1-cyclohexen-1-yl)phenoxy]acetic acid (500 mg) is dissolved by stirring and warming with 0.25 N sodium bicarbonate solution (5.4 ml). The solution is diluted to 10 ml and sterilized by filtration. All the water that is used in the preparation is pyrogen-free. The concentration of the active agent in the final solution is 5%.

Similar parenteral solutions can be prepared by replacing the active ingredient of this Example by any of the other compounds of this invention.

EXAMPLE 31

| Dry-Filled Capsules Containing 100 mg of Active Ingredient Per Capsule | |
|---|---|
| | Per Capsule |
| [2,3-Dichloro-4-(5-methyl-3-oxo-1-cylcohexen-1-yl)phenoxy]acetic acid | 100 mg |
| Lactose | 99 mg |
| Magnesium Stearate | 1 mg |
| Capsule (Size No. 1) | 200 mg |

[2,3-Dichloro-4-(5-methyl-3-oxo-1-cyclohexen-1-yl)phenoxy]acetic acid is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredient of this Example by any of the other compounds of this invention.

What is claimed is:

1. A compound of the formula:

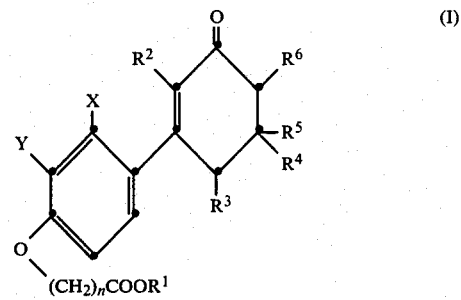

wherein:

$R^1$ is hydrogen, lower alkyl, branched or unbranched, containing from 1 to 5 carbon atoms, or a carboxyalkyl group containing from 2 to 6 carbon atoms;

$R^2$, $R^6$ are each independently hydrogen or lower alkyl, branched or unbranched, containing from 1 to 5 carbon atoms;

$R^3$ is hydrogen, lower alkyl, branched or unbranched, containing from 1 to 5 carbon atoms, cycloalkyl containing from 3 to 6 nuclear carbon atoms, or aryl;

$R^4$, $R^5$ are each independently hydrogen, lower alkyl containing from 1 to 5 carbon atoms, aralkyl, aryl, or halo substituted aryl;

X, Y are each independently hydrogen, halo or lower alkyl containing from 1 to 5 carbon atoms; and n is 1 to 4;

or the pharmaceutically acceptable salts or derivatives thereof.

2. A compound of the formula:

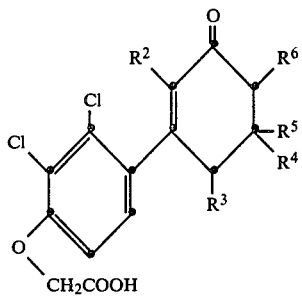

wherein:

R², R³, R⁴, R⁵, R⁶ are each independently hydrogen or lower alkyl, branched or unbranched, containing from 1 to 5 carbon atoms; or the pharmaceutically acceptable salts or derivatives thereof.

3. A compound according to claim 1, which is [2,3-dichloro-4-(3-oxo-1-cyclohexen-1-yl)phenoxy]acetic acid;

[2,3-dichloro-4-(6-methyl-3-oxo-1-cyclohexen-1-yl)phenoxy]acetic acid;

[2,3-dichloro-4-(4-methyl-3-oxo-1-cyclohexen-1-yl)phenoxy]acetic acid;

[2,3-dichloro-4-(5-methyl-3-oxo-1-cyclohexen-1-yl)phenoxy]acetic acid;

[2,3-dichloro-4-(2-methyl-3-oxo-1-cyclohexen-1-yl)phenoxy]acetic acid;

[2,3-dichloro-4-(4,5-dimethyl-3-oxo-1-cyclohexen-1-yl)phenoxy]acetic acid;

[2,3-dichloro-4-(5,5-dimethyl-3-oxo-1-cyclohexen-1-yl)phenoxy]acetic acid;

[2,3-dichloro-4-(2,5-dimethyl-3-oxo-1-cyclohexen-1-yl)phenoxy]acetic acid;

[2,3-dichloro-4-(5-ethyl-3-oxo-1-cyclohexen-1-yl)phenoxy]acetic acid;

[2,3-dichloro-4-(6-ethyl-3-oxo-1-cyclohexen-1-yl)phenoxy]acetic acid;

ethyl [2,3-dichloro-4-(6-ethyl-3-oxo-1-cyclohexen-1-yl)phenoxyacetate;

1-carboxy-1-methylethyl [2,3-dichloro-4-(6-ethyl-3-oxo-1-cyclohexen-1-yl)phenoxy]acetate;

[2,3-dichloro-4-(6-ethyl-3-(hydroxyimino)-1-cyclohexen-1-yl)phenoxy]acetic acid hemitoluene solvate;

4-[2,3-dichloro-4-(6-ethyl-3-oxo-1-cyclohexen-1-yl)phenoxy]butyric acid;

[3-chloro-4-(6-ethyl-3-oxo-1-cyclohexen-1-yl)phenoxy]acetic acid;

[2,3-dichloro-4-(6-ethyl-4-methyl-3-oxo-1-cyclohexen-1-yl)phenoxy]acetic acid;

[2,3-dichloro-4-(6-ethyl-5-methyl-3-oxo-1-cyclohexen-1-yl)phenoxy]acetic acid;

[2,3-dichloro-4-(6-propyl-3-oxo-1-cyclohexen-1-yl)phenoxy]acetic acid;

[2,3-dichloro-4-(6-cyclopentyl-3-oxo-1-cyclohexen-1-yl)phenoxy]acetic acid;

[2,3-dichloro-4-(5-phenyl-3-oxo-1-cyclohexen-1-yl)phenoxy]acetic acid;

[2,3-dichloro-4-(5-(4-fluorophenyl)-3-oxo-1-cyclohexen-1-yl)phenoxy]acetic acid;

[2,3-dichloro-4-(5-(2-fluorophenyl)-3-oxo-1-cyclohexen-1-yl)phenoxy]acetic acid;

ethyl [2,3-dichloro-4-(5-methyl-3-oxo-1-cyclohexen-1-yl)phenoxy]acetate;

1-carboxy-1-methylethyl [2,3-dichloro-4-(5-methyl-3-oxo-1-cyclohexen-1-yl)phenoxy]acetate.

4. A compound according to claim 3, which is a pure diasteriomer.

5. A compound according to claim 4, which is the (+)-enantiomer.

6. A compound according to claim 4, which is the (−)-enantiomer.

7. A compound which is (+) [2,3-dichloro-4-(5-methyl-3-oxo-1-cyclohexen-1-yl)phenoxy]acetic acid.

8. A compound which is (−) [2,3-dichloro-4-(5-methyl-3-oxo-1-cyclohexen-1-yl)phenoxy]acetic acid.

9. A pharmaceutical composition useful in the treatment of brain injury which comprises a pharmaceutical carrier and an effective amount of a compound of claim 1.

10. A pharmaceutical composition according to claim 9, which comprises a pharmaceutical carrier and an effective amount of a compound according to claim 3.

11. A method of treating a person with brain injury which comprises administering to such a person an effective amount of a compound of claim 1.

12. A method according to claim 11, which comprises administering to a person with brain injury an effective amount of the pharmaceutical composition of claim 10.

13. A method according to claim 11, which comprises administering to a person with brain injury an effective amount of a compound according to claim 3.

* * * * *